United States Patent [19]

Edwards

[11] Patent Number: 4,575,569

[45] Date of Patent: Mar. 11, 1986

[54] ALKOXYLATION OF THIOLS IN THE PRESENCE OF A REACTION PROMOTER

[75] Inventor: Charles L. Edwards, Houston, Tex.

[73] Assignee: Shell Oil Company, Houston, Tex.

[21] Appl. No.: 621,316

[22] Filed: Jun. 15, 1984

[51] Int. Cl.[4] ........................................... C07C 148/00
[52] U.S. Cl. ......................................... 568/45; 568/55
[58] Field of Search ..................................... 568/45, 55

[56] References Cited

U.S. PATENT DOCUMENTS

| | | | |
|---|---|---|---|
| 2,129,709 | 9/1938 | Schuette | 260/151 |
| 2,494,610 | 1/1950 | Davidson et al. | 260/609 |
| 2,565,986 | 8/1951 | Olin | 260/609 |
| 2,570,050 | 10/1951 | Eby | 260/609 |
| 2,637,701 | 5/1953 | Doerr | 252/351 |
| 2,642,400 | 6/1953 | Harris | 568/45 |
| 3,030,426 | 4/1962 | Moseley | 260/615 |
| 3,053,903 | 9/1962 | Holland | 260/615 |
| 3,174,900 | 3/1965 | Wyant | 167/58 |
| 3,440,287 | 4/1969 | Horsley | 260/609 |
| 3,538,033 | 11/1970 | Hayashi et al. | 260/29.2 |
| 3,988,378 | 10/1976 | Wirth | 260/609 |

FOREIGN PATENT DOCUMENTS 49-54312  5/1974  Japan.

OTHER PUBLICATIONS

Derwent Abstract of Japanese Kokai 54312 (1974).

Primary Examiner—Donald G. Daus
Assistant Examiner—Mary E. Ceperley

[57] ABSTRACT

Thiol alkoxylates having utility, for instance, an nonionic surfactants in detergent formulations are prepared by the reaction of alkane thiols with alkylene oxides in the presence of a catalytically effective amount of one or more basic alkoxylation catalysts and additionally in the presence of as a reaction promoter added thiol alkoxylate having in the alkoxylate molecule from one to about 30 adducts of one or more alkylene oxides. The presence of the added thiol alkoxylate promoter improves the handling of the reaction mixture and facilitates the production of thiol alkoxylates having low content of polyalkylene glycol byproduct.

23 Claims, No Drawings

ALKOXYLATION OF THIOLS IN THE PRESENCE OF A REACTION PROMOTER

BACKGROUND OF THE INVENTION

This invention relates to the preparation of thiol alkoxylates by the addition reaction of alkylene oxides with thiols. More specifically, this invention is directed to an improved process for conducting the alkoxylation reaction of alkane thiols with alkylene oxides in the presence of certain basic catalysts and certain reaction promoters.

Under conventional practice, thiol alkoxylates have been typically prepared by the reaction of alkylene oxides with alkane thiols in the presence of either acid or base catalysts. In the particular case of the preparation of a thiol ethoxylate (represented by formula III below) the addition of a number (n) of ethylene oxide molecules (formula II) to a single thiol molecule (formula I) is illustrated by the equation

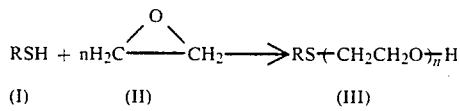

$$RSH + nH_2C\overset{O}{-\!\!-\!\!-}CH_2 \longrightarrow RS(CH_2CH_2O)_nH$$

(I)     (II)                (III)

wherein R is alkyl and n is an integer equal to or greater than one. The product of any such alkoxylation reaction is a mixture of various thiol alkoxylate molecules having a variety of alkylene oxide adducts, i.e., a mixture of compounds with different values of n.

Thiol alkoxylates are known materials having recognized utility as surfactants and as intermediates in the synthesis of other organic compounds. Thiol alkoxylates in which the alkyl group has a number of carbon atoms in the detergent range, i.e., from about 8 to 20, have attracted particular interest, for instance as components of commercial detergent formulations and as spermicidal agents.

The present invention is directed to improvement in the thiol alkoxylate preparation process which utilizes certain basic catalysts, particularly certain alkali and alkaline earth metal catalysts. In one aspect, this improvement specifically relates to enhanced selectivity of the alkoxylation reaction for the desired thiol alkoxylates. In the presence of the basic catalysts, alkylene oxides tend to react to form polyalkylene glycols, for example, polyethylene glycols of the formula HO(CH$_2$CH$_2$O)$_y$H, wherein y is an integer greater than 1. The formation of these byproducts not only represents a loss of alkylene oxide reactant but also results in an alkoxylate product of lower quality. In another aspect, the invention is directed to improvements relating to the processing and handling of the alkoxylation reaction mixture. Under common conventional practice, the catalyst is mixed with the liquid thiol reactant and this mixture is then contacted with the gaseous alkylene oxide reactant. The alkali and alkaline earth metal catalysts (or the compounds to which they are converted in the presence of thiol) are insoluble in the thiol reactant, even at typically low catalyst concentrations. The heterogeneous mixtures which result tend to interfere with processing, for instance, by plugging transfer lines to the alkoxylation reactor and fouling heat transfer surfaces.

SUMMARY OF THE INVENTION

In accordance with the present invention, the reaction of a thiol reactant with an alkylene oxide reactant for the preparation of a thiol alkoxylate product is carried out in the presence of a basic catalyst selected from compounds of the alkali and alkaline earth metals and additionally in the presence of a specified reaction promoter. Very advantageously, the promoter is an addition reaction product of the thiol and the alkylene oxide reactants, or, in other words, a thiol alkoxylate of the sort prepared by the process of the invention. The presence of even very small amounts of the promoter in the mixture of catalyst and thiol reactant facilitates its handling by eliminating formation of a separate insoluble catalyst phase. Moreover, making use of the promoter provides improved selectivity from the standpoint of utilization of the alkylene oxides in thiol alkoxylate production, as opposed to polyalkylene glycol byproduct formation.

Accordingly, the present invention is a process for the preparation of thiol alkoxylates which comprises reacting a thiol reactant comprising one or more alkane thiols with an alkylene oxide reactant comprising one or more alkylene oxides in the presence of a catalytically-effective amount of one or more basic alkoxylation catalysts, and additionally in the presence of as reaction promoter one or more added thiol alkoxylates as are produced by the alkoxylation reaction of an alkane thiol and an alkylene oxide.

DESCRIPTION OF THE PREFERRED EMBODIMENTS

The present invention relates to discoveries associated with promoting an alkoxylation reaction between alkane thiols and alkylene oxides catalyzed by alkali or alkaline earth metal catalysts. Apart from aspects directed to the use of certain specified reaction promoters, the process of the invention is as a general rule suitably conducted under such processing procedures and reaction conditions as are known to the art of base-catalyzed alkoxylation reactions.

Still, for purposes of the invention, particular preferences may be stated for certain processing parameters. For instance, the alkoxylation reaction is preferably carried out at a temperature in the range from 0° to 220° C. Because the addition of the first alkylene oxide unit to the thiol molecule proceeds more readily than the subsequent reaction of additional alkylene oxide units, a staging of the reaction temperature may be desirable. Thus, in a particularly preferred process, temperature is initially maintained between about 10° and 100° C. and then increased, e.g., to between about 100° and 200° C., as necessary to maintain the desired rate of reaction. Considered most preferred is a process temperature which is initially in the range from about 10° C. to 50° C. and is increased as the reaction proceeds to a temperature in the range from about 100° to 150° C. Although the pressure under which the alkoxylation reaction is conducted is not critical to the invention, a total pressure in the range from about 0 to 150 psig is preferred.

Under preferred conditions of temperature and pressure the thiol reactant and the thiol alkoxylate reaction promoter are generally liquid and the alkylene oxide reactant a vapor. The alkoxylation reaction is conducted by contacting the gaseous alkylene oxide with a mixture of the catalyst and the promoter in the thiol. Addition is typically made of the alkylene oxide to a reactor containing the liquid mixture, with the rate of addition, and thus also the process pressure, controlled to maintain the desired reaction rate.

Since, as is known, there is a danger of explosion in alkylene oxides maintained in concentrated form at elevated temperature and pressure, the partial pressure of the alkylene oxide in the vapor phase is preferably limited, for instance, to less than about 60 psia, and this reactant is diluted with an inert gas such as nitrogen, for instance, to a vapor phase concentration of about 50 percent or less. The reaction can, however, be safely accomplished at greater alkylene oxide concentration, greater total pressure and/or greater partial pressure of alkylene oxide if suitable precautions, known to the art, are taken to manage the risks of explosion. A total pressure of between about 40 and 100 psig, with an alkylene oxide partial pressure between about 15 and 70 psia, is particularly preferred, while a total pressure of between about 50 and 80 pisg, with an alkylene oxide partial pressure between about 20 and 50 psia is considered more preferred.

The thiol reactant that is suitable for use in practice of the present invention comprises, in the broad sense, one or more of the alkane thiols as have heretofore been recognized as suitable for alkoxylation by reaction with alkylene oxides in the presence of basic catalysts. Alkane thiols in the 6 to 30 carbon number range are particularly preferred reactants for the preparation of thiol alkoxylates for use as surface active agents, while those in the 7 to 20 carbon number range are considered more preferred and those in the 8 to 15 carbon number range most preferred.

The thiol reactant molecule is suitably either primary, secondary, or tertiary and of either linear, branched, or cyclic carbon structure. Specific examples of suitable tertiary thiols are those having a highly branched carbon chain which are derived via hydrosulfurization of the products of the oligomerization of lower olefins, particularly those dimers, trimers, and tetramers and pentamers of propylene and the butylenes. Secondary thiols are exemplified by the lower alkane thiols, such as 2-propanethiol, 2-butanethiol, and 3-pentanethiol, as well as by the products of the hydrosulfurization of the substantially linear oligomers of ethylene as are produced by the Oxo process. Representative, but by no means limiting, examples of thiols derived from ethylene oligomers include the linear carbon chain products, such as 2-decanethiol, 3-decanethiol, 4-decanethiol, 5-decanethiol, 3-dodecanethiol, 5-dodecanethiol, 2-hexadecanethiol, 5-hexadecanethiol, and 8-octadecanethiol, and the branched carbon chain products, such as 2-methyl-4-tridecanethiol. Primary thiols are typically prepared from terminal olefins by hydrosulfurization under free-radical conditions and include, for example, 1-butanethiol, 1-hexanethiol, 1-dodecanethiol, and 1-tetradecanethiol and 2-methyl-1-tridecanethiol. The invention is also suitably applied using polythiol reactants, having multiple -SH groups, although monothiolic reactants are preferred. Particular preference exists for a reactant consisting essentially of one or more secondary and tertiary thiols.

The alkylene oxide (epoxide) reactant utilized in the process of the invention preferably comprises one or more of the several alkylene oxides known for use in alkoxylation reactions with thiols and other compounds having active hydrogen atoms. Particularly preferred are the vicinal alkylene oxides having from 2 to 4 carbon atoms, including ethylene oxide, 1,2-propylene oxide, and the 1,2- and 2,3-butylene oxides. Mixtures of alkylene oxides are suitable in which case the product will be a mixed thiol alkoxylate. Thiol alkoxylates prepared from ethylene or propylene oxides are recognized to have very advantageous surface active properties and for this reason there is particular preference in practice of the invention for a reactant consisting essentially of ethylene oxide and/or propylene oxide. A reactant consisting essentially of ethylene oxide is considered most preferred for use in the invention.

The relative quantity of thiol and alkylene oxide reactants is not critical to the invention, although it will determine the average alkylene oxide number of the alkoxylate product. In many of the uses made of thiol alkoxylates, an adduct number in the range from about 3 to 20, particularly from about 5 to 12 is preferred. Accordingly, preference can be expressed in the practice of the invention for a molar ratio of alkylene oxide reactant to thiol reactant which is in the range from about 3 to 20, particularly from about 5 to 12.

The alkoxylation reaction of the process of the invention is intended to be carried out in the presence of a basic alkoxylation catalyst, particularly an alkali or alkaline earth metal catalyst. The alkali and alkaline earth metal alkoxylation catalysts are known to include lithium, sodium, potassium, rubidium, cesium, magnesium, calcium, strontium, and barium. Suitable catalysts include the elemental metals as well as certain of their compounds, particularly the oxides, hydroxides, carbonates, acetates, hydrides, alcoholates, and mercaptides. It is generally believed in the art that in either case the active form of the catalyst is a mercaptide or other species which results from reaction of the alkali metal compound with the thiol and/or with the thiol alkoxylate promoter.

When a compound is utilized as catalyst for the alkoxylation reaction it is known to be desirable to remove by-products which result from reaction between the catalyst and the thiol and/or alkylene oxide reactants. This is particularly true when the presence of water in the alkoxylation mixture results from the use of an oxide or hydroxide catalyst. The presence of water is known to promote the conversion of alkylene oxides to polyalkylene glycols. Water removal is very conveniently accomplished in the course of practice of this invention by its evaporation from the mixture, preferably at an elevated temperature, e.g., 100° C. or greater, and/or with the aid of vacuum or an inert gas sparge. Although complete removal of water is not critical to the invention, it is generally the case that the selectivity of the alkoxylation reaction is enhanced as the water content of the mixture is decreased. Lowering the water content of the reaction mixture to less than about 50 ppm is preferable, while still lower water content, e.g., less than about 40 ppm and particularly less than about 35 ppm, is more preferred. Without intention of limiting the invention to one theory of operation, it is thought that the action of the promoter in enhancing selectivity of the thiol alkoxylation reaction for the process of the invention may relate, at least in part, to facilitating removal of water and/or other deleterious components from the reaction system.

Particularly preferred basic catalysts for purposes of this invention are the alkali metals and their compounds. Potassium and sodium oxides and hydroxides are considered most preferred. The catalyst is present in the reaction mixture in an effective amount. Catalyst concentrations between about 0.10 and 5% by weight (% W), based on thiol reactant, are preferred, and concentrations between about 0.15 and 1.0 % W are considered most preferred.

The alkoxylation process of the invention is necessarily carried out in the presence of specified reaction promoter. Like the thiol alkoxylate product of the process of the invention, the promoter comprises one or more compounds of the general formula $R'-S(C_xH_{2x}-O)_nH$. For purposes of defining suitable promoters, $R'$ is as an alkyl group of one to 30 carbon atoms, inclusive, n represents an integer in the range from 1 to about 30, and x (in each individual $-C_xH_{2x}-O-$ moiety) is an integer, preferably in the range from 2 to 4, inclusive. In alternative terms, the promoter is described as the alkoxylation reaction product of one or more $C_1$ or $C_{30}$ alkane thiols with from one to about 30 moles of one or more alkylene oxides.

In the course of the alkoxylation reaction of the process of the invention, the thiol alkoxylate promoter as well as the thiol reactant reacts with the alkylene oxide reactant. For reasons relating to properties of the process product mixture, the (higher) alkoxylate formed by reaction of the (lower) alkoxylate promoter with alkylene oxide is subject to the same preferences, in terms of carbon number of the alkyl group and alkylene oxide adduct number, as is the thiol alkoxylate formed during practice of the invention by reaction of the thiol reactant with the alkylene oxide reactant. (Consideration is given to the contribution of such higher thiol alkoxylates of the promoter to properties of the process product mixture because it is in most cases impractical to separate this higher alkoxylate from the principal product formed through alkoxylation of the thiol reactant.) Thus, the carbon number of the alkyl group $R'$ is preferably in the range from about 6 to 30, more preferably in the range from about 7 to 20, and most preferably in the range from about 8 to 15. Expressed in another manner, the promoter comprises one or more alkoxylation products of thiols which are preferably in the $C_6$ to $C_{30}$ range, more preferably in the $C_7$ to $C_{20}$ range and most preferably in the $C_8$ to $C_{15}$ range. It is particularly desirable that in the practice of the invention, the carbon number (or carbon number distribution) of the alkyl $R'$ group of the thiol alkoxylate promoter be essentially the same as that of the thiol reactant utilized. In order to obtain a product mixture in which the higher thiol alkoxylate formed from the promoter has an adduct number distribution similar to that of the thiol alkoxylate formed from the thiol reactant, activators of relatively low adduct number, for instance, a promoter characterized by an average adduct number less than 5, are preferred. More preferred are promoters having an average adduct number less than about 3, while promoters having an average adduct number less than about 2 are considered most preferred. Again, as indicated above, these preferences relate to desired properties of the product and not to the operability in the use of the materials as reaction promoters for purpose of invention.

The source of the promoter and the manner in which it is introduced into the reactant and catalyst mixture are not critical to the invention. The promoter is itself preferably, but not necessarily, prepared via a process in accordance with this invention.

The amount of thiol alkoxylate promoter present during contact between the thiol and alkylene oxide reactants and the catalyst is not critical to the invention. It has been found convenient to express the amount of promoter used in terms of catalyst present. In these terms, preferences can be expressed for a quantity of promoter between about 10 and 2000% m (percent by mole) based on catalyst, while a quantity between about 20 and 1000% m is more preferred and a quantity between about 50 and 700% m is most preferred. If an alkali metal or alkali metal compound is used as catalyst, particular preference can be expressed for a quantity of promoter between about 50 and 500% m based on mols of alkali metal. If an alkaline earth metal or compound is used as catalyst, particular preference can be expressed for a quantity of promoter between 100 and 700% m, based on mols of alkaline earth metal. Best results are obtained when the promoter is added in sufficient quantity to solubilize the catalyst in the reaction mixture. Typically, this is an amount which, on a molar basis, is roughly equal to (e.g., 0.5 to 1.5 times) that of the alkali metal catalyst or is roughly twice (e.g. 1 to 3 times) that of the alkaline earth metal catalyst.

In terms of processing procedures, the invention is preferably carried out by mixing together the basic catalyst (or a catalyst precursor), the liquid thiol reactant and the liquid thiol alkoxylate promoter and then contacting the resulting solution with gaseous alkylene oxide reactant at the specified temperature and pressure. In one preferred mode of operation, the catalyst and the promoter are first mixed before thay are contacted with either of the reactants. If, on the other hand, the catalyst and thiol alkoxylate promoter are individually introduced into the reaction mixture it is preferred that the promoter be put into solution in the liquid reactant phase in the specified quantity before the catalyst is mixed into this liquid phase. Addition of reaction mixture components in this sequence minimizes or prevents the formation of a solid catalyst phase at any time during the process.

Following the preparation of the mixture of the catalyst, the promoter and the thiol in the desired relative quantities the mixture is contacted at suitable process temperature and pressure with the alkylene oxide reactant. The alkoxylation reaction generally commences without a significant induction period. As the alkylene oxide is taken up in the reaction, additional alkylene oxide is added, conveniently at a rate which maintains an approximately constant reaction rate. Addition of alkylene oxide and its reaction with thiol to form thiol alkoxylate is continued until the product reaches the average alkylene oxide adduct number desired for the particulr process. Generally, although not necessarily, the invention is best utilized in the preparation of thiol alkoxylates having an average adduct number in the range of between about 1 to 30, expressed in terms of the total mols of alkylene oxide reacted per mol of thiol. For reasons relating to utility of the thiol alkoxylate in the broadest commercial applications, the process is continued to yield a product having an average adduct number that is preferably between about 2 and 20, more preferably between about 3 and 15, most preferably between about 4 and 12. The time required to complete a process in accordance with the invention in the presence of the specified catalyst and promoter, is dependent both upon the degree of alkoxylation that is desired (i.e., upon the average adduct number of the product) as well as upon the rate of the alkoxylation reaction. This reaction rate is, in turn, dependent upon such parameters as reaction temperature, pressure, and catalyst concentration in the reaction mixture. Under most preferred operating conditions, preparation of an alkoxylate having an average alkylene oxide adduct number of about 3 can typically be accomplished in about 1 to 2 hour, while preparation of a product having an average adduct number of about 12 would require about 4 to 6 hours. These reaction times are merely illustrative and can be substantially reduced by operation at the higher reaction temperatures and/or pressures, although often at the expense of a loss of selectivity in the utilization of the reactants to the desired thiol alkoxylate products.

Following the reaction process, the product mixture is usually neutralized by addition of an acid to convert the basic catalyst components to inactive neutral salts. The choice of the acid used is not critical. Examples of suitable acids known to the art for this service include acetic acid, sulfuric acid, phosphoric acid, and hydrochloric acid. Acetic acid is generally preferred.

The invention is further illustrated by the following examples.

EXAMPLE 1

An alkoxylation reaction in accordance with the invention was conducted in a 300 ml autoclave reactor. The thiol reactant utilized was a mixture of secondary thiols which had been derived via the hydrosulfurization of a mixture of essentially linear olefins having 11 to 12 carbon atoms. Ethylene oxide was employed as the alkylene oxide reactant. The catalyst was potassium hydroxide.

For use as reaction promoter there was prepared a thiol ethoxylate of a low ethylene oxide adduct number by the following procedure.

First, 0.1 gram of 85 percent purity potassium hydroxide (1.5 millimoles KOH) was added to 54.5 grams (281 millimoles) of the $C_{11}$ and $C_{12}$ thiol reactant in a multineck round bottom flask. The resulting mixture was heated to 130° C. and sparged with nitrogen at 130° C. for 1 hour, and then transferred to the autoclave reactor maintained under a nitrogen atmosphere. The reactor was heated to about 30° C. and pressurized by addition of nitrogen and the gaseous ethylene oxide to a total pressure of about 30 psig (35 psia nitrogen and 10 psia ethylene oxide). As the ethoxylation reaction commenced, ethylene oxide was added at a rate sufficient to maintain constant total pressure in the system. Over a 9 minute period, 12.4 grams (281 millimoles) of ethylene oxide were added. Ethylene oxide addition was then discontinued and the reaction mixture maintained at 30° C. for an additional 30 minutes to consume remaining unreacted ethylene oxide. The mixture was cooled to 25° C., transferred under nitrogen to a sample bottle and neutralized with acetic acid to a pH of 6.0. Gas chromatographic analysis indicated a product containing no residual thiol reactant and 99% w of thiol alkoxylate (ethoxylate) molecules having an average adduct number of about 1.0.

For example 1 alkoxylation in accordance with the invention was carried out by blending 50 grams of thiol reactant with 5 grams of the thiol alkoxylate promoter prepared as described above. The resulting mixture was heated under a nitrogen atmosphere to 100° C. at which time 0.83 grams of 85% w purity KOH was added. On a molar basis, the blend contained about 166% m promoter, calculated on catalyst. The catalyst concentration was about 1.4% w, calculated on thiol reactant. The thiol reactant/catalyst/promoter mixture was heated with nitrogen sparging for 60 minutes at 130° C. for removal of water. The mixture was then transferred to the autoclave reactor, sealed, brought to a temperature of 30° C. and pressurized to a total pressure of about 30 psig (35 psia nitrogen and 10 psia ethylene oxide). After the initial addition of approximately one mole of ethylene oxide per mole of thiol reactant, the reaction was continued at 125° C. and 60 psig total pressure (45 psia nitrogen and 30 psia EO) until a total of 85.6 grams of ethylene oxide had been added to the reaction mixture. The mixture was maintained at 125° C. for an additional 30 minutes. The product mixture, after cooling to 25° C. and neutralization to a pH of 6.5, was a clear pale yellow product having an average ethylene oxide adduct number of 6.9. Analysis of the product showed that it contained no residual thiol and only 2.3% w polyethylene glycols (PEG).

EXAMPLES 2–5

A series of alkoxylation reactions in accordance with the invention was carried out following the general procedure of Example 1.

In Example 2, a mixture consisting of 50 grams of thiol reactant, 5 grams of thiol alkoxylate promoter (with an average adduct number of 1.0) and 0.68 grams of 85% w purity KOH catalyst was reacted with ethylene oxide. A total of 61.2 grams (1.39 mols) of ethylene oxide was added over a period of about 1.5 hours to give a product having an average adduct number of 5.0. The product contained no residual thiol and only 3.4% w PEG.

In Example 3, a mixture consisting of 50 grams of thiol reactant, 5 grams of thiol alkoxylate promoter (with an average adduct number of 1.0) and 0.99 grams of 85% w purity KOH catalyst was reacted with ethylene oxide. A total of 113.8 grams (2.59 mols) of ethylene oxide was added over a period of about 2 hours to give a product having an average adduct number of 8.8 and containing no thiol and 2.4% w PEG.

In Example 4, a mixture consisting of 40 grams of thiol reactant, 5 grams of thiol alkoxylate promoter (with an average adduct number of 1.0) and 0.97 grams of 85% w purity KOH catalyst was reacted with ethylene oxide. A total of 129.8 grams (2.95 mols) of ethylene oxide was added over a period of about 2.5 hours to give a product having an average adduct number of 12.2 and containing no thiol and 2.2% w PEG.

In Example 5, a mixture consisting of 40 grams of thiol reactant, 5 grams of thiol alkoxylate promoter (with an average adduct number of 1.0) and 1.22 grams of 85% w purity KOH catalyst was reacted with ethylene oxide. A total of 163 grams (3.7 mols) of ethylene oxide was added over a period of about 3.5 hours producing a product having an average adduct number of 15.2 and containing no thiol and 2.5% w PEG.

Comparative Example

A comparative example, not in accordance with the invention, was carried out to illustrate the influence of the added thiol alkoxylate reaction promoter upon thiol alkoxylation process performance. A $C_{12}$ secondary thiol derived from predominantly linear olefins by hydrosulfurization was reacted with ethylene oxide. The general procedures of Example 1 were again followed, with the exception that no thiol alkoxylate promoter was added to the reaction mixture. Dry thiol reactant (42.7 grams, 0.211 mols) was mixed with 85% purity potassium hydroxide (0.4 grams, 0.006 mols) and the mixture heated with nitrogen sparging for ninety minutes at 130° C. A nonhomogeneous mixture resulted, with a solid phase adhering to equipment surfaces.

Ethylene oxide (40% m in nitrogen) was initially contacted with the thiol reactant/catalyst mixture at a temperature of 30° C. and a pressure of about 30 psig. Reaction temperature was increased to 125° C. after 17 minutes and maintained at that temperature for another 198 minutes. Pressure was increased as the reaction proceeded (to about 55 psig) to maintain rate.

The reaction consumed a total of 55.7 grams (1.27 moles) of ethylene oxide to produce a thiol ethoxylate having an average adduct number of 5.3. The product had an undesirably high PEG content of 5.3% w.

EXAMPLES 6–9

Another series of alkoxylation reactions in accordance with the invention was carried out following the procedure of Example 1. A mixture of essentially linear $C_{10}$ secondary thiols was substituted as thiol reactant. The thiol alkoxylate promoter was a $C_{10}$ thiol ethoxylate having an average adduct number of about 1.0. In each example, the blend of thiol reactant and thiol ethoxylate promoter contained 50 grams of thiol reactant and 5 grams of thiol ethoxylate having an average adduct number of about 1.0.

For example 6, total of 67.8 grams (1.54 mols) of ethylene oxide was reacted with the thiol to yield a thiol ethoxylate having an average adduct number of 4.6, and containing no thiol and 2.1% w PEG.

In Example 7, a total of 95.5 grams (2.17 mols) of ethylene oxide reacted with the thiol over a period of about 1 hour to yield a thiol ethoxylate having an average adduct number of 6.8, and containing no thiol and 3.0% w PEG.

In Example 8, a total of 116 grams (2.64 mols) of ethylene oxide was consumed in producing an ethoxylate producing having an average adduct number of 8.6, and containing no thiol and 2.5% of PEG.

In Example 9, a total of 170 grams (3.88 mols) of ethylene oxide was consumed in producing a thiol ethoxylate having an adduct number of 11.9 and containing 3.3% w PEG.

EXAMPLE 10

A process in accordance with the invention was carried out following the procedures of Example 1, but using as reactant a mixture of essentially linear $C_{13}$ and $C_{14}$ secondary thiols. The thiol alkoxylate promoter was an ethoxylate of $C_{13}/C_{14}$ thiols, and the blend of thiol reactant and thiol ethoxylate promoter contained 40 grams of thiol reactant and 5 grams of thiol ethoxylate having an average adduct number of about 1.0.

A total of 129.8 grams (2.95 mols) of ethylene oxide was reacted with the thiol over a period of 2.5 hours to yield a thiol ethoxylate having an average adduct number of 11.8 and containing 3.6% w PEG.

EXAMPLES 11 AND 12

Two alkoxylation reactions in accordance with the invention were carried out following procedures of Example 1, but using a mixture of essentially linear $C_8$ secondary thiols and a promotor which was an ethoxylate of the same $C_8$ thiols. The blend of thiol reactant and thiol ethoxylate promoter in Example 11 contained 50 grams of thiol reactant and 5 grams of promoter having an average adduct number of about 1.0. A total of 61.6 grams (1.4 mols) of ethylene oxide was reacted over a period of 1 hour to yield a product having an average adduct number of 3.8 and a PEG content of 3.6% w.

In Example 12, the blend of thiol reactant and thiol ethoxylate promoter contained 45 grams of thiol and 10 grams of promoter having an average adduct number of about 1.0. A total of 92.1 grams (2.1 mols) of ethylene oxide was reacted over a period of 1.5 hours to yield a product having an average adduct number of 6.0 and a PEG content of 4.2% w.

EXAMPLE 13

The process of the invention was utilized according to the following procedures to prepare a tertiary thiol ethoxylate.

For the preparation of a tertiary thiol ethoxylate promoter, 50 grams (0.248 8mols) of a $C_{12}$ tertiary thiol (a commercial product of the Pennwalt Corporation) and 0.1 grams of 85% potassium hydroxide (0.0015 mols KOH) were charged to a 100 ml glass flask. The mixture was heated to 130° C. under a nitrogen sparge, and sparging with stirring was continued for one hour at that temperature. The thiol and catalyst mixture was then transferred to a 300 ml autoclave. A 40% m/60% m mixture of ethylene oxide and nitrogen was introduced into the autoclave for ethoxylation of the thiol at a temperature of 50° C. and under a pressure of 30 psig. After an equimolar quantity of ethylene oxide had been added to the thiol, the flow of this reactant was discontinued and the autoclave maintained at 50° C. for one additional hour. The product mixture, 59.4grams of a clear, colorless liquid, was cooled and neutralized with acetic acid to a pH of 6.5. Analysis indicated a 99% yield of tertiary ethoxylate, calculated on thiol, and a polyethylene glycol content of 0.2% w.

The product mixture of this preparation, which had an average adduct number of 1.0, was then utilized as promoter in a thiol ethoxylation process in accordance with the invention. To a 100 ml glass flask were added 55 grams (0.272 mols) of the commercial $C_{12}$ tertiary thiol, 0.88 grams of 85% w potassium hydroxide (0.013 mols) and 5 grams (0.020 mols) of the tertiary $C_{12}$ thiol ethoxylate promoter. The mixture was sparged with nitrogen for one hour at 130° C. to evaporate water, and then charged to the autoclave reactor. Ethylene oxide (40% m in nitrogen) was introduced as the alkylene oxide reactant. The ethoxylation reaction was initially conducted at 35° C. and 30 psig until roughly one mole of ethylene oxide, per mole of thiol had been consumed. The reaction was then continued at 100° C. and 60 psig until a total of 90 grams of ethylene oxide had been added to the autoclave, and the mixture thereafter maintained for one additional hour at 100° C. The product mixture, after cooling to 25° C. and neutralization to a pH of 6.5, was a pale yellow, clear product having an average ethylene oxide adduct number of 7.3 and containing 1.2% w PEG.

Comparative Example

An attempt was made, not in accordance with the invention, to ethoxylate a thiol in the presence of a reaction promoter but in the absence of a basic alkoxylation catalyst. For this purpose, 35 grams (0.173 mols) of a commercial $C_{12}$ tertiary thiol was mixed with 15 grams (0.016 mols) of a thiol ethoxylate promoter having an average adduct number of 1.0. (This promoter had been prepared from the same $C_{12}$ tertiary thiol by ethoxylation in the presence of a KOH catalyst and neutralization of the product with acetic acid.) The thiol reactant and promoter mixture was sparged with nitrogen at 130° C. for one hour and then transferred under nitrogen to a 300 ml autoclave reactor. Ethylene oxide (40% m in nitrogen) was introduced at a pressure of 60 psig and the autoclave was then maintained at 120° C. for two hours. No reaction was detected. Analysis confirmed that the reaction mixture contained only starting materials and no thiol ethoxylate.

What is claimed is:

1. A process for the preparation of thiol alkoxylates which comprises (a) mixing (i) a secondary thiol reactant comprising one or more secondary $C_6$ to $C_{30}$ alkane thiols, (ii) a catalytically effective amount of a basic alkoxylation catalyst selected from the group consisting of alkali and alkaline earth metal oxides and hydroxides and mixture thereof, and (iii) between about 10 and 2000 percent by mole, based on catalyst, one or more thiol alkoxylates as are produced by the alkoxylation reaction of $C_6$ to $C_{30}$ alkane thiols and $C_2$ to $C_4$ alkylene oxides, (b) evaporating water from the resulting mixture, and (c) contacting the mixture, following water evaporation, with an alkylene oxide reactant comprising one or more $C_2$ to $C_4$ alkylene oxides.

2. The process of claim 1, wherein the alkylene oxides are selected from the group consisting of ethylene oxide and propylene oxide.

3. The process of claim 2, wherein the quantity of thiol alkoxylates mixed with alkane thiol reactant and basic alkoxylation catalyst in step (a) is between about 20 and 1000 percent by mole, calculated on mols of basic alkoxylation catalyst.

4. The process of claim 3, wherein the thiol alkoxylates have an average alkylene oxide adduct number less than 5.

5. The process of claim 4, wherein the evaporation step is conducted under conditions sufficient to lower the water content of the mixture to less than about 50 ppm by weight.

6. The process of claim 5, wherein water is evaporated by heating the mixture of thiol reactant, catalyst, and promoter to a temperature in excess of 100° C.

7. The process of claim 6, wherein the mixture is heated under sparging with an inert gas or under vacuum.

8. The process of claim 7, wherein the mixture is heated to a temperature of at least 20° C. under sparging with nitrogen for at least 10 minutes.

9. The process of claim 8, wherein the quantity of thiol alkoxylates mixed with alkane thiol reactant and basic alkoxylation catlyst in step (a) is between about 50 and 700 percent by mole, calculated on mols of basic alkoxylation catalyst.

10. The process of claim 9, wherein the basic alkoxylation catalyst is selected from the group consisting of the oxides and hydroxides of sodium and potassium, the quantity of thiol alkoxylates in the mixture of step (a) is between about 50 and 500 percent by mol, and the thiol alkoxylates have an average alkylene oxide adduct number less than 5.

11. A process for the preparation of thiol alkoxylates which comprises (a) mixing (i) a secondary thiol reactant comprising one or more secondary $C_6$ to $C_{30}$ alkane thiols, (ii) a catalytically effective amount of one or more basic alkoxylation catalysts, and (iii) between about 10 and 2000 percent by mole, based on catalyst, of one or more thiol alkoxylates as are produced by the alkoxylation reaction of $C_6$ to $C_{30}$ alkane thiols and $C_2$ to $C_4$ alkylene oxides, and (b) contacting the mixture with an alkylene oxide reactant comprising one or more $C_2$ to $C_4$ alkylene oxides.

12. The process of claim 11, wherein the basic alkoxylation catalyst is selected from the group consisting of alkali and alkaline earth metal oxides and hydroxides and mixtures thereof.

13. The process of claim 12, wherein the alkylene oxides are selected from the group consisting of ethylene oxide and propylene oxide.

14. The process of claim 13, wherein the quantity of thiol alkoxylates mixed with alkane thiol reactant and basic alkoxylation catalyst in step (a) is between about 20 and 1000 percent by mole, calculated on moles of basic alkoxylation catalyst.

15. The process of claim 14, wherein the thiol alkoxylates have an average alkylene oxide adduct number less than 5.

16. The process of claim 15, wherein the one or more basic alkoxylation catalysts are selected from the group consisting of the oxides and hydroxides of sodium and potassium.

17. The process of claim 16, wherein the quantity of thiol alkoxylates mixed with alkane thiol reactant and basic alkoxylation catalyst in step (a) is between about 50 and 500 percent by mole, calculated on moles of catalyst.

18. In a process for the preparation of thiol alkoxylates which comprises steps for (a) mixing a thiol reactant comprising one or more $C_6$ to $C_{30}$ alkane thiols with a catalytically-effective amount of one or more basic alkoxylation catalysts and (b) contacting the resulting mixture with an alkylene oxide reactant comprising one or more alkylene oxide compounds, wherein the mixture of the thiol reactant and the one or more basic alkoxylation catalysts in step (a) is characterized as a heterogeneous mixture, the improvement which comprises admixingin step (a) the thiol reactant and the one or more basic alkoxylation catalysts with between about 10 and 2000 percent by mole, calculated on moles of catalyst, of one or more thiol alkoxylates as are produced by the alkoxylation reaction of $C_6$ to $C_{30}$ alkane thiols with alkylene oxide.

19. The process of claim 18, wherein the one or more basic alkoxylation catalysts are selected from the group consisting of alkali and alkaline earth metal oxides and hydroxides and mixtures thereof.

20. The process of claim 19, wherein the thiol reactant consists essentially of one or more alkane thiols having carbon numbers in the range from about 8 to 18, inclusive, the alkylene oxide reactant consists essentially of one or more alkylene oxides selected from the group consisting of ethylene oxide and propylene oxide, and the one or more admixed thiol alkoxylates are as produced by the alkoxylation reaction of $C_8$ to $C_{18}$ alkane thiols with ethylene oxide, propylene oxide or mixtures thereof.

21. The process of claim 20, wherein the quantity of thiol alkoxylates admixed with the thiol reactant and the one or more catalysts is sufficient to solubilize the one or more catalysts in the mixture.

22. The process of claim 21 which additionally comprises a process step for evaporating water from the mixture of thiol reactant, catalyst and thiol alkoxylate before contacting this mixture with alkylene oxide reactant in step (b).

23. The process of claim 22, wherein the basic alkoxylation catalyst is selected from the group consisting of the oxides and hydroxides of sodium and potassium.

* * * * *